United States Patent [19]

Kida

[11] Patent Number: 6,075,162
[45] Date of Patent: Jun. 13, 2000

[54] INTEGRATED METHOD FOR PRODUCING METHYL METHACRYLATE AND HYDROGEN CYANIDE

[75] Inventor: Koichi Kida, Ibaraki-ken, Japan

[73] Assignee: Mitsubishi Gas Chemical Company, Inc., Tokyo, Japan

[21] Appl. No.: 09/260,000

[22] Filed: Mar. 2, 1999

[30] Foreign Application Priority Data

Mar. 11, 1998 [JP] Japan .................................. 10-059732

[51] Int. Cl.$^7$ .......................... C07C 67/30; C07C 67/20; C07C 253/00
[52] U.S. Cl. ......................... 560/212; 560/215; 560/187; 558/332
[58] Field of Search .................................... 560/212, 215, 560/187; 523/368; 558/332

[56] References Cited

U.S. PATENT DOCUMENTS 5,371,273  12/1994  Shima et al. .

FOREIGN PATENT DOCUMENTS 1-290653  11/1989  Japan .

*Primary Examiner*—Gary Geist
*Assistant Examiner*—Robert W. Deemie
*Attorney, Agent, or Firm*—Antonelli, Terry, Stout & Kraus, LLP

[57] ABSTRACT

A method of producing methyl methacrylate comprises Step 1 of producing acetone cyanhydrin from hydrogen cyanide and acetone; Step 2 of producing α-hydroxyisobutyramide by hydrating acetone cyanhydrin; Step 3 of producing methyl α-hydroxyisobutyrate and ammonia by a reaction of α-hydroxyisobutyramide and methanol; Step 4 of producing methyl methacrylate by dehydrating methyl α-hydroxyisobutyrate; and Step 5 of producing hydrogen cyanide in vapor phase by reacting methanol and the ammonia obtained in Step 3 over a solid catalyst in the presence of molecular oxygen. By using methanol in the step 3, the conversion ratio of α-hydroxyisobutyramide into methyl α-hydroxyisobutyrate can be increased because the equilibrium of the reaction is easily sifted toward the product side by removing ammonia being produced from the reaction system. The use of methanol in the step 3 produces additional advantages of efficiently linking the steps to eliminate the steps for separation and purification, thereby reducing the production cost.

Step 1:

$$HCN + CH_3COCH_3 \rightarrow (CH_3)_2(OH)CN;$$

Step 2:

$$(CH_3)_2C(OH)CN + H_2O \rightarrow (CH_3)_2(OH)CONH_2$$

Step 3:

$$(CH_3)_2C(OH)CONH_2 + CH_3OH \rightarrow (CH_3)_2(OH)CO_2CH_3 + NH_3$$

Step 4:

$$(CH_3)_2C(OH)CO_2CH_3 \rightarrow (CH_2)_2=C(CH_3)CO_2CH_3 + H_2O$$

Step 5:

$$CH_3OH + NH_3 + O_2 \rightarrow HCN + 3H_2O$$

5 Claims, No Drawings

INTEGRATED METHOD FOR PRODUCING METHYL METHACRYLATE AND HYDROGEN CYANIDE

BACKGROUND OF THE INVENTION

The present invention relates to a novel method of producing methyl methacrylate from acetone and methanol as the starting materials. Methyl methacrylate is one of the industrially most important intermediate materials and has been used in a great amount as a starting material for various types of polymers.

Known methods currently employed in industrially producing methyl methacrylate include ACH (acetone cyanhydrin) method in which methyl methacrylate is synthesized through ACH produced from hydrogen cyanide (prussic acid) and acetone; a modified ACH method; C4 oxidation method using isobutylene or t-butyl alcohol as the starting material; etc. In addition, an oxidative dehydrogenation of isobutyric acid, a dehydration by condensing formaldehyde with propionic acid or propionaldehyde, an ammoxydation of isobutylene, etc. have been proposed.

The C4 oxidation method involves many side reactions to detrimentally decrease the yield of methyl methacrylate and increase a cost for purification, and requires a complicated, expensive production apparatus. Additional disadvantage of the C4 oxidation method is that the supply of the starting materials such as isobutylene and t-butyl alcohol is subject to limitation. An oxyesterification in which the oxidation and esterification of methacrolein occur simultaneously has been proposed as a modified method for the C4 oxidation method. However, the basic problems mentioned above still remain unsolved. Also, a method including an addition reaction of carbon monoxide and methanol to methylacetylene has been proposed. However, it is difficult to supply the starting material in an amount enough to practice the method in industrial scale.

In the ACH method, methyl methacrylate is produced by reacting, in the presence of an excess amount of concentrated sulfuric acid, methanol and ACH synthesized from hydrogen cyanide and acetone. Since the respective reactions can be easily controlled and the yield of methyl methacrylate is relatively high, the ACH method is still widely used. However, this method accompanies a large amount of waste sulfuric acid and by-produced ammonium sulfate which increase a cost of producing methyl methacrylate. To eliminate this drawback, Japanese Patent Laid-Open No. 1-290653 proposes a modified ACH method in which the use of sulfuric acid catalyst is avoided, i.e., no ammonium sulfate is by produced. The proposed, modified ACH method comprises the following five steps:

Step (1) of producing acetone cyanhydrin from hydrogen cyanide and acetone according to the following reaction,

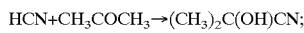
HCN+CH$_3$COCH$_3$→(CH$_3$)$_2$C(OH)CN;

Step (2) of producing α-hydroxyisobutyramide by hydrating acetone cyanhydrin according to the following reaction,

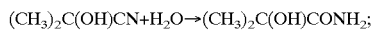
(CH$_3$)$_2$C(OH)CN+H$_2$O→(CH$_3$)$_2$C(OH)CONH$_2$;

Step (3) of producing methyl α-hydroxyisobutyrate and formamide by a reaction of α-hydroxyisobutyramide and methyl formate according to the following reaction,

(CH$_3$)$_2$C(OH)CONH$_2$+HCOOCH$_3$→(CH$_3$)$_2$C(OH)COOCH$_3$+ HCONH$_2$;

Step (4) of producing methyl methacrylate by dehydrating methyl α-hydroxyisobutyrate according to the following reaction,

(CH$_3$)$_2$C(OH)COOCH$_3$→CH$_2$=C(CH$_3$)COOCH$_3$ +H$_2$O;

and

Step (5) of producing hydrogen cyanide by dehydrating formamide according to the following reaction,

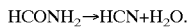
HCONH$_2$→HCN+H$_2$O.

The proposed method is excellent because the yield of each step is relatively high, the reaction apparatus scarcely needs to be corrosion-resistant, and hydrogen cyanide is reproduced. However, the conversion rate of the step (3) is as low as 50% because it is an equilibrium reaction, thereby to necessitate additional steps for separating and recycling the non-reacted α-hydroxyisobutyramide and methyl formate. Therefore, a large-sized apparatus is required and a utility cost is increased. In addition, since the dehydration of formamide in the step (5) should be carried out under reduced pressure, a vacuum apparatus is required to increase an energy cost.

OBJECT AND SUMMARY OF THE INVENTION

Accordingly, an object of the present invention is to provide a novel method of producing methyl methacrylate in which the problems in the known methods, particularly in the improved ACH method, are solved.

As a result of the intense research for improving the improved ACH method, particularly the steps (3) and (5) thereof, the inventor has found that an inexpensive method of producing methyl methacrylate can be achieved by replacing the reactions of the steps (3) and (5) of the modified ACH method with other reactions thereby to efficiently linking the respective production steps.

Thus, the present invention provides a method of producing methyl methacrylate comprising:

(1) Step 1 of producing acetone cyanhydrin from hydrogen cyanide and acetone according to the following reaction,

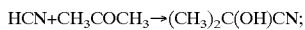
HCN+CH$_3$COCH$_3$→(CH$_3$)$_2$C(OH)CN;

(2) Step 2 of producing α-hydroxyisobutyramide by hydrating acetone cyanhydrin according to the following reaction,

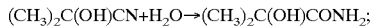
(CH$_3$)$_2$C(OH)CN+H$_2$O→(CH$_3$)$_2$C(OH)CONH$_2$;

(3) Step 3 of producing methyl α-hydroxyisobutyrate and ammonia by a reaction of α-hydroxyisobutyramide and methanol according to the following reaction,

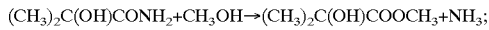
(CH$_3$)$_2$C(OH)CONH$_2$+CH$_3$OH→(CH$_3$)$_2$C(OH)COOCH$_3$+NH$_3$;

(4) Step 4 of producing methyl methacrylate by dehydrating methyl α-hydroxyisobutyrate according to the following reaction,

(CH$_3$)$_2$C(OH)COOCH$_3$→CH$_2$=C(CH$_3$)COOCH$_3$+H$_2$O;

and (5) Step 5 of producing hydrogen cyanide in vapor phase by reacting the ammonia obtained in the step 3 and methanol over a solid catalyst in the presence of molecular oxygen according to the following reaction,

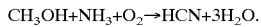
CH$_3$OH+NH$_3$+O$_2$→HCN+3H$_2$O.

The use of cheap methanol in the step 3 of the above production method in place of methyl formate used in the known modified ACH method results in the following advantages. First, ammonia being produced in the step 3 is easily removed from the reaction system (liquid phase) to shift the equilibrium to the product side, because ammonia has the lowest boiling point among the chemical species involved in the step 3. Therefore, α-hydroxyisobutyramide is converted to methyl α-hydroxyisobutyrate in a high conversion rate, this reducing or avoiding the necessity of recycling non-reacted starting compounds. Even when an excess amount of methanol is used in the step 3, the non-reacted, residual methanol can be easily recovered together with ammonia by distillation and supplied directly to the step 5, thereby making the separation of ammonia in a high purity unnecessary. In addition, the dehydration of methyl α-hydroxyisobutyrate in the step 4 is preferably conducted in the presence of methanol, and therefore, it is not needed to separate methanol from methyl α-hydroxyisobutyrate during the recovery thereof by distillation in the step 3. With the above advantages, the utility cost and facility cost can be reduced. Since the step 5 for producing hydrogen cyanide (prussic acid) can be conducted under ordinary pressure or higher, the utility cost and facility cost can be further reduced. As described above, the modified ACH method has been improved drastically by using methanol in place of methyl formate in the step 3. It has not been known in the art that an inexpensive method of producing methyl methacrylate can be attained by replacing the reactions of some production steps with other reactions, thereby efficiently linking the steps as mentioned above.

DETAILED DESCRIPTION OF THE INVENTION

The step 1 for producing ACH by a reaction between hydrogen cyanide (prussic acid) and acetone is conducted under known conditions as taught in Japanese Patent Laid-Open No. 1-290653, for example, by mixing both the compounds in the presence of an alkali catalyst, amine catalyst, etc. The reaction proceeds quantitatively to produce ACH in a high yield. In a preferred embodiment, ACH is efficiently produced by absorbing a hydrogen cyanide-containing gas produced by ammoxydation of methanol in the step 5 into acetone.

In the step 2, α-hydroxyisobutyramide is produced by reacting ACH with water in the presence of a catalyst, for example, in the same manner as taught in Japanese Patent Laid-Open No. 1-290653. A catalysts effective for hydrating the nitriles may be used in the step 2, and preferably an oxide of metal such as manganese, copper, nickel, etc., more preferably manganese dioxide. The charged amount ratio of ACH to water is suitably 10:90 to 90:10 by weight. The additional use of a solvent such as acetone, methanol, etc. is effective in view of obtaining more preferred effect. When using manganese dioxide as the catalyst, the reaction temperature is preferably 20–150° C., and more preferably 40–120° C. The reaction time is preferably 0.3–6 hours, and more preferably 0.5–3 hours. The reaction may be carried out in any manner of batch method, semi-batch method and continuous method.

In the step 3, methyl α-hydroxyisobutyrate is produced by reacting α-hydroxyisobutyramide and methanol under boiling condition or pseudo-boiling condition attained by bubbling inert gas into the reaction mixture, while distilling ammonia away from the reaction system by heating in the presence of a homogeneous liquid catalyst. Alternatively, methyl α-hydroxyisobutyrate is formed by reacting α-hydroxyisobutyramide and methanol under boiling condition over a heterogeneous solid catalyst, while simultaneously distilling ammonia away from the system. In this step, the yield of methyl α-hydroxyisobutyrate depends on the rapid removal of ammonia from the reaction system, the reaction temperature and the type of catalyst.

The reaction temperature is preferably 80–250° C., this creating a self-exerting pressure, i.e., a pressure due to a vapor pressure of the reaction liquid and a pressure exerted by the coexisting gas, of ordinary pressure to 5 MPa, and the reaction time is 0.2–10 hours. The weight ratio of α-hydroxyisobutyramide to methanol each being charged is not critical in the present invention, and preferably 2:1 to 1:20. The homogeneous catalyst may be a metal catalyst capable of dissolving into the reaction liquid and may include an alkali metal alkolate and an organometallic compound of titanium, tin, aluminum, etc., preferably an alkolate of titanium or tin such as titanium tetraisopropoxide, tin tetrabutoxide, etc. The heterogeneous solid catalyst is preferably basic, and a basic ion-exchanging resin, magnesia, calcium oxide, etc. may be used in the form of slurry or shaped article. Generally, the heterogeneous catalyst is less efficient as compared with the homogeneous catalyst.

The reaction of the step 3 is characterized by a high conversion rate of α-hydroxyisobutyramide as high as 60% or more due to a rapid removal of ammonia from the reaction system and an easy recovery of methyl α-hydroxyisobutyrate by a simple distillation because of the absence of formamide by-produced in the known modified ACH method. In addition to the above advantage, the non-reacted methanol and methyl α-hydroxyisobutyrate are not needed to separate from each other, and are preferably distilled together to be supplied directly to the next step 4 of dehydration.

The dehydration of methyl α-hydroxyisobutyrate to methyl methacrylate in the step 4 may be carried out by a known method taught by Japanese Patent Laid-Open No. 1-290653, etc. For example, methyl α-hydroxyisobutyrate is dehydrated by a liquid phase reaction in the presence of a catalyst such as sulfuric acid, phosphoric acid, etc. However, a vapor phase reaction over a solid catalyst is more preferred in view of efficiency. The vapor-phase catalytic reaction using the solid catalyst such as silica, silica-alumina, zeolite, solid phosphoric acid, etc. may be carried out under ordinary pressure at 200–500° C. During the reaction, steam or inert gas may be introduced into the reaction system to prevent the carbon deposition onto the catalyst. It is preferred to carry out the reaction in the presence of methanol to avoid the hydrolysis of the methyl ester. For this reason, the separation of methanol and methyl α-hydroxyisobutyrate is not required in the step 3.

In the step 5, hydrogen cyanide (prussic acid) is produced by vapor-phase ammoxydation in the presence of a solid catalyst at 300–550° C., preferably 400–500° C. using methanol and ammonia from the step 3, preferably ammonia generated in the step 3 and the non-reacted methanol in the step 3, as the starting materials while introducing an oxygen-containing gas, usually air. The molar ratio of ammonia/methanol and the molar ratio of oxygen/methanol are not strictly limited, and preferably 0.1 to 5 for ammonia/methanol and 0.1 to 5 for oxygen/methanol. Metal oxides usually used in ammoxydation or metal oxides used for oxidizing methanol may be used in this step as the catalyst. Specifically, vanadium oxide, molybdenum oxide, iron oxide, copper oxide, tin oxide and chromium oxide may be preferably used alone or in combination. The reaction is carried out in a reaction vessel having a fixed bed or a fluidized bed. The reaction vessel should be equipped with a cooling means because the reaction is highly exothermic. After washing the resulting gas containing hydrogen cyanide from the reaction vessel with an aqueous solution of mineral acid such as sulfuric acid, etc. to remove the non-reacted ammonia, the gas is condensed and then distilled to recover hydrogen cyanide, which is then reacted with acetone in the step 1. However, it is preferred to supply the gas washed with an aqueous solution of mineral acid directly into the step 1 to bring it into contact with acetone to produce ACH in view of efficiency.

The present invention will be further described while referring to the following Examples which should be considered to illustrate various preferred embodiments of the present invention.

EXAMPLE 1

Step 1 Synthesis of ACH from hydrogen cyanide and acetone

In a 500 ml-flask equipped with a stirrer, a thermometer and a dropping funnel for adding hydrogen cyanide, charged were 116 g of acetone and 1 ml of 1N aqueous solution of sodium hydroxide. Then, 59.4 g of hydrogen cyanide were added dropwise while maintaining the mixture in the flask at 20° C. After the addition of hydrogen cyanide, the mixture was kept at 20° C. for 2 hours to complete the reaction. Then, the mixture was adjusted to pH 3 by adding 50% sulfuric acid. The flask was connected to a vacuum line and the non-reacted hydrogen cyanide was distilled away from the reaction system under reduced pressure to obtain 171 g of ACH with a purity of 98.4% in a yield of 99% based on the amount of acetone.

Step 2 Synthesis of α-hydroxyisobutyramide by hydrating ACH

In a 1-liter flask equipped with a stirrer, a reflux condenser and a thermometer, a mixture of 63.2 g of potassium permanganate and 500 g of water was heated to 70° C. under stirring. Then, 240 g of an aqueous solution dissolving 96.2 g of manganese sulfate and 40 g of 15% sulfuric acid were added to the mixture and the contents were kept at 70° C. for 3 hours to proceed the reaction. After cooling the contents, the precipitate was filtered off with suction and washed with 2.4 liters of water. The cake of the precipitate was dried overnight at 60° C. to obtain 74 g of activated manganese dioxide, which was used as the catalyst for the subsequent reaction.

Into a 1-liter flask equipped with a stirrer, a reflux condenser and a thermometer, successively charged were 150 g of acetone cyanhydrin obtained in the step 1,350 g of water, 100 g of acetone and 60 g of manganese dioxide. The contents were kept at 60° C. for 5 hours under stirring to proceed the reaction. After cooling with ice, the resulting solution was filtered with suction to remove the catalyst. As a result of gas chromatographic analysis on the filtrate, it was found that the conversion rate of ACH was 99.5%, the yield of α-hydroxyisobutyramide was 95%, and small amounts of acetone and formaldehyde were present in the filtrate. The filtrate was distilled under reduced pressure to obtain, as the main distillate, 155 g α-hydroxyisobutyramide with a purity of 99.5% or more.

Step 3 Synthesis of methyl α-hydroxyisobutyrate from α-hydroxyisobutyramide and methanol Into a 1-liter stainless autoclave equipped with a stirrer, charged were 103.6 g of α-hydroxyisobutyramide obtained in the step 2.96 g of methanol and 10 g of titanium tetraisopropoxide (Ti(O-isoPr)$_4$). The contents were heated under stirring and maintained at 180° C. for 2 hours under a self-exerting pressure of 1.9 MPa to carry out the reaction while distilling off the ammonia. After cooling, the reaction product was subjected to gas chromatographic analysis to show that the conversion rate of α-hydroxyisobutyramide was 81% and the selectivity of methyl α-hydroxyisobutyrate based on α-hydroxyisobutyramide was 94%.

Step 4 Synthesis of methyl methacrylate by dehydrating methyl α-hydroxyisobutyrate A mixture of 20 g of sodium dihydrogenphosphate and 80 g of water was added with 60 g of silica gel (16–24 mesh) available from Fuji Silysia Chem., Ltd. After water was distilled away from the mixture under reduced pressure, the residue was dried overnight at 150° C. to prepare a catalyst to be used in the subsequent reaction. After placing 10 g of the catalyst in a quartz reaction tube (14 mm inner diameter× 40 mm length) equipped with a vaporizer, the quartz reaction tube was heated in an electric furnace while regulating the temperature of the catalyst layer within 400° C. or lower. A 2:1 mixture by mole of methanol and methyl α-hydroxyisobutyrate obtained in the step 3 was continuously supplied to the vaporizer in a rate of 10 g/hour by using a metering pump. The mixture was vaporized there and the vapor was supplied to the catalyst layer to conduct the reaction for 10 hours in total. The result of the analysis on the resulting product showed that the conversion rate of methyl α-hydroxyisobutyrate was 99%, the yield of the target methyl methacrylate based on the charged amount of methyl α-hydroxyisobutyrate was 88%, and the yield of methacrylic acid, as another useful compound, was 6.8%.

Step 5 Production of hydrogen cyanide by ammoxydation of methanol

Separately, 25 g of ferric nitrate (iron (III) nitrate) nonahydrate and 3.64 g of ammonium molybdate were added with 50 ml distilled water to prepare respective aqueous solutions. The aqueous ammonium molybdate solution was added to the aqueous ferric nitrate solution at room temperature under vigorous stirring to obtain a uniform catalyst solution, which was then sprinkled over 271 g of carrier which was prepared by calcining activated alumina (8–14 mesh) at 1300° C. for 20 hours to impregnate the carrier with the catalyst solution. After drying at 120° C. for 48 hours in a drier to thoroughly remove the water, the impregnated catalyst was calcined at 500° C. for 16 hours in an air stream to obtain a catalyst. The catalyst was charged into a SUS316 reaction tube having an inner diameter of 18 mm in a volume of 10 ml. The starting gas having molar ratios of 1.2 for ammonia/methanol and 2.5 for oxygen in air/methanol was continuously passed through the reaction tube at a space velocity SV of 4000/hr to carry out the reaction at 420–430° C. under atmospheric pressure (ordinary pressure) for 10 hours. The result of gas chromatographic analysis on the resulting gas showed that the yield of hydrogen cyanide based on the reacted methanol was 92%, the yield of hydrogen cyanide based on the reacted ammonia was 90%, and carbon dioxide and carbon monoxide were by produced.

As described above, the use of methanol in place of methyl formate extremely increases the conversion rate of α-hydroxyisobutyramide into methyl α-hydroxyisobutyrate because ammonia being generated can be easily removed from the reaction system, thereby sifting the equilibrium toward the product side. In addition, by the use of methanol, the step 3 for producing methyl α-hydroxyisobutyrate and the step 4 for dehydrating methyl α-hydroxyisobutyrate into methyl methacrylate are efficiently linked because the separation of methanol from methyl α-hydroxyisobutyrate is not required prior to the step 4. Likewise, the step 3 and the step 5 for reproducing hydrogen cyanide are efficiently linked because methanol and ammonia distilled off in the step 3 can be used as the starting materials in the step 4. Thus, the method of producing methyl methacrylate according to the present invention is industrially advantageous.

What is claimed is:

1. A method of producing methyl methacrylate comprising Step 1 of producing acetone cyanhydrin from hydrogen cyanide and acetone; Step 2 of producing α-hydroxyisobutyramide by hydrating acetone cyanhydrin, Step 3 of producing methyl α-hydroxyisobutyrate and ammonia by a reaction of α-hydroxyisobutyramide and methanol; Step 4 of producing methyl methacrylate by dehydrating methyl α-hydroxyisobutyrate; and Step 5 of producing hydrogen cyanide in vapor phase by reacting methanol and the ammonia obtained in Step 3 over a solid catalyst in the presence of molecular oxygen.

2. The method according to claim 1, wherein the reaction of said step 3 is carried out at 80–250° C. under a self-exerting pressure of ordinary pressure to 5 MPa for 0.2–10 hours in the presence of a homogeneous liquid catalyst or a heterogeneous solid catalyst, said self-exerting pressure being a combination of a vapor pressure exerted by a reaction liquid and a pressure exerted by a coexisting gas.

3. The method according to claim 1, wherein the reaction of said step 3 is carried out while removing ammonia being generated from a reaction system so that the equilibrium of said reaction is shifted toward a production side.

4. The method according to claim 1, wherein the ammoxydation of said step 5 is carried out at 300–550° C.

5. The method according to claim 1, wherein the ammoxydation of said step 5 is carried out under ordinary pressure.

* * * * *